United States Patent
Lalleman et al.

(10) Patent No.: US 10,010,495 B2
(45) Date of Patent: *Jul. 3, 2018

(54) HAIR DYEING PROCESS USING AT LEAST ONE ORTHO-DIPHENOL AND ONE ORGANIC SALT OF TITANIUM AND OF A CARBOXYLIC ACID

(71) Applicant: L'OREAL, Paris (FR)

(72) Inventors: Boris Lalleman, Paris (FR); Alain Lagrange, Coupvray (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/104,121

(22) PCT Filed: Dec. 10, 2014

(86) PCT No.: PCT/EP2014/077224
§ 371 (c)(1),
(2) Date: Jun. 13, 2016

(87) PCT Pub. No.: WO2015/086677
PCT Pub. Date: Jun. 18, 2015

(65) Prior Publication Data
US 2016/0317412 A1    Nov. 3, 2016

(30) Foreign Application Priority Data

Dec. 13, 2013  (FR) ...................................... 13 62579

(51) Int. Cl.
| *A61Q 5/10* | (2006.01) |
| *A61K 8/49* | (2006.01) |
| *A61K 8/29* | (2006.01) |
| *A61K 8/34* | (2006.01) |
| *A61K 8/365* | (2006.01) |
| *A61K 8/97* | (2017.01) |
| *A61K 8/22* | (2006.01) |
| *A61K 8/362* | (2006.01) |
| *A61K 8/58* | (2006.01) |

(52) U.S. Cl.
CPC ................ *A61K 8/498* (2013.01); *A61K 8/22* (2013.01); *A61K 8/29* (2013.01); *A61K 8/347* (2013.01); *A61K 8/362* (2013.01); *A61K 8/365* (2013.01); *A61K 8/58* (2013.01); *A61K 8/97* (2013.01); *A61Q 5/10* (2013.01); *A61K 2800/4324* (2013.01); *A61K 2800/58* (2013.01); *A61K 2800/884* (2013.01)

(58) Field of Classification Search
CPC . A61Q 5/10; A61K 8/58; A61K 8/362; A61K 8/22; A61K 8/498; A61K 2800/4324; A61K 2800/58; A61K 2800/884
See application file for complete search history.

(56) References Cited

U.S. PATENT DOCUMENTS

| 3,376,110 | A | 4/1968 | Shiraeff |
| 4,823,985 | A | 4/1989 | Grollier et al. |
| 5,008,093 | A | 4/1991 | Merianos |
| 5,183,901 | A | 2/1993 | Login et al. |
| 7,081,485 | B2 | 7/2006 | Suh et al. |
| 7,833,290 | B2 | 11/2010 | Guerin et al. |
| 2003/0103917 | A1 | 6/2003 | Pruche |
| 2003/0163878 | A1 | 9/2003 | Pruche |
| 2008/0233068 | A1* | 9/2008 | Forbes ................... A61K 8/25 424/70.1 |
| 2010/0146718 | A1 | 6/2010 | Guerin et al. |
| 2010/0154143 | A1* | 6/2010 | Guerin ................... A61K 8/19 8/424 |
| 2012/0110751 | A1* | 5/2012 | Blackburn ............ A61K 8/19 8/421 |
| 2013/0139846 | A1 | 6/2013 | Rondot et al. |

FOREIGN PATENT DOCUMENTS

| DE | 19859721 A1 | 6/2000 |
| EP | 2196188 A2 | 6/2010 |
| EP | 2438900 A1 | 4/2012 |
| FR | 2586913 A1 | 3/1987 |
| FR | 2814943 A1 | 4/2002 |
| FR | 2814945 A1 | 4/2002 |
| FR | 2814946 A1 | 4/2002 |
| FR | 2814947 A1 | 4/2002 |
| FR | 2928086 A1 | 9/2009 |
| FR | 2951374 A1 | 4/2011 |
| FR | 2976793 A1 | 12/2012 |
| FR | 2976797 A1 | 12/2012 |
| WO | 2006/106366 A1 | 10/2006 |
| WO | 2010/135237 A1 | 11/2010 |
| WO | 2011/000892 A2 | 1/2011 |
| WO | 2011/045404 A2 | 4/2011 |
| WO | 2011/086282 A1 | 7/2011 |
| WO | 2011/086284 A1 | 7/2011 |
| WO | 2012/175683 A2 | 12/2012 |
| WO | 2015/086678 A1 | 6/2015 |

OTHER PUBLICATIONS

STIC Search Report dated Nov. 25, 2016.*
International Search Report for PCT/EP2014/077224, dated Mar. 11, 2015.
International Search Report for PCT/EP2014/077225, dated Mar. 11, 2015.

* cited by examiner

*Primary Examiner* — Eisa B Elhilo
(74) *Attorney, Agent, or Firm* — The Marbury Law Group, PLLC

(57) ABSTRACT

The present invention relates to a process for dyeing keratin fibers, in particular human keratin fibers such as the hair, in which the said fibers are treated using one or more cosmetic compositions comprising a) one or more ortho-diphenols, b) one or more organic salts of titanium and of at least one carboxylic acid, and c) optionally one or more chemical oxidizing agents such as hydrogen peroxide or one or more hydrogen peroxide generating systems.

20 Claims, No Drawings

HAIR DYEING PROCESS USING AT LEAST ONE ORTHO-DIPHENOL AND ONE ORGANIC SALT OF TITANIUM AND OF A CARBOXYLIC ACID

CROSS REFERENCE TO RELATED APPLICATIONS

This is a national stage application of PCT/EP2014/077224, filed internationally on Dec. 10, 2014, which claims priority to French Application No. 1362579, filed on Dec. 13, 2013, both of which are incorporated by reference herein in their entireties.

The present invention relates to a process for dyeing keratin fibres, in particular human keratin fibres such as the hair, in which the said fibres are treated using one or more cosmetic compositions comprising a) one or more ortho-diphenols, b) one or more salts of titanium and of an organic acid, in particular a carboxylic acid, and c) optionally one or more chemical oxidizing agents such as hydrogen peroxide or one or more hydrogen peroxide generating systems.

It is known practice to obtain "permanent" colourings with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation. It is also known that the shades obtained may be varied by combining these oxidation bases with couplers or colouring modifiers, the latter being chosen especially from aromatic meta-diamines, meta-aminophenols, meta-diphenols and certain heterocyclic compounds such as indole compounds. This oxidation dyeing process consists in applying to the keratin fibres bases or a mixture of bases and couplers with hydrogen peroxide ($H_2O_2$ or aqueous hydrogen peroxide solution), as oxidizing agent, in leaving it to diffuse, and then in rinsing the fibres. The colorations resulting therefrom are permanent, strong and resistant to external agents, especially to light, bad weather, washing, perspiration and rubbing.

However, the commercial hair dyes that contain them generally have the drawback of staining clothing, of leading to odour and comfort problems, and of degrading keratin fibres. This is particularly the case with oxidation dyes.

In the field of dyeing, it is also known practice to dye keratin materials such as the hair or the skin using ortho-diphenol compounds in the presence of a metal salt especially of manganese (Mn) and/or zinc (Zn). In particular, patent applications FR 2 814 943, FR 2 814 945, FR 2 814 946 and FR 2 814 947 propose compositions for dyeing the skin or keratin fibres, comprising a dye precursor that contains at least one ortho-diphenol, Mn and/or Zn oxides and salts, alkaline agents of hydrogen carbonate type in a particular Mn, Zn/hydrogen carbonate ratio and optionally an enzyme. According to these documents, it is possible to obtain colourings of keratin materials with atmospheric oxygen or any oxygen-generating system.

However, the colourings obtained are not strong enough or intense enough, and/or are not very persistent, especially in the case of hair fibres.

Moreover, it is known practice to use metals at acidic pH for dyeing keratin fibres in amounts similar to those employed for dyes using a mordanting process, which consists in preparing the fibres before performing the dyeing operation in order to obtain fast shades (*Ullmann's Encyclopaedia* "Metal and Dyes", 2005 § 5.1, p. 8).

However, this process generally has the drawback of not always respecting the cosmetic nature of the keratin fibre.

Other documents describe the use of ortho-diphenols in combination with Mn and Zn salts and other metal salts, including titanium salts, and a chemical oxidizing agent (FR 297 673, WO2011/086284, WO2011/086282 and FR 2 951 374).

Nevertheless, improvements should be further made, especially in terms of persistence of the colour with regard to shampooing and to sweat.

There is thus a real need to develop dyeing processes for obtaining stronger and/or more persistent colourings using ortho-diphenols, especially using natural extracts that are rich in ortho-diphenols and less aggressive to keratin fibres. In particular, there is a need to obtain colourings that satisfactorily withstand external agents (light, bad weather, shampooing or sweat), which are persistent and homogeneous, i.e. showing little dyeing selectivity between the root and the end, while at the same time remaining strong and/or chromatic.

This (these) aim(s) are achieved by the present invention, one subject of which is a process for dyeing keratin fibres, in particular human keratin fibres such as the hair, in which the said fibres are treated, in one or more steps, with one or more cosmetic compositions containing, taken together or separately in the said composition(s), the following ingredients:

a) one or more ortho-diphenols;
b) one or more organic titanium salts, in particular in which the titanium has the oxidation state 2, 3 or 4, denoted Ti(II), Ti(III) or Ti(IV), preferably Ti(IV);
b1) optionally one or more carboxylic acids of formula (I) below:

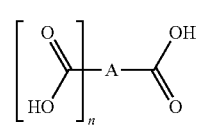

(I)

formula (I) or a salt thereof, in which:

A represents a monovalent group when n has the value zero or a polyvalent group when n is greater than or equal to 1, saturated or unsaturated, cyclic or non-cyclic and aromatic or non-aromatic hydrocarbon-based group comprising from 1 to 50 carbon atoms which is optionally interrupted with one or more heteroatoms and/or optionally substituted, in particular with one or more hydroxyl groups; preferably, A represents a monovalent ($C_1$-$C_6$)alkyl group or a polyvalent ($C_1$-$C_6$)alkylene group optionally substituted with one or more hydroxyl groups;

n represents an integer between 0 and 10 inclusive; preferably, n is between 0 and 5, such as between 0 and 2;

c) optionally, one or more chemical oxidizing agents chosen especially from hydrogen peroxide and one or more hydrogen peroxide generating systems;

it being understood that at least one of the compositions used in the dyeing process is at acidic pH, i.e. less than 7.0, particularly less than 5, more particularly at a pH of between 0 and 4 inclusive, preferably between 0.5 and 3.5, more preferably between 1 and 3.

Preferably, the composition(s) used in the process of the invention are aqueous.

Another subject of the invention is a cosmetic composition comprising the ingredients a), b) and optionally c) as defined previously.

Another subject of the present invention relates to a multi-compartment device comprising ingredients a), b), c) and optionally d) as defined herein after, distributed in several compartments.

The multi-compartment device or "kit" is suitable for performing the dyeing process according to the invention.

The process according to the invention has the advantage of dyeing human keratin fibres, with persistent dyeing results. In particular, the dyeing process according to the invention makes it possible to produce colourings that are resistant to washing, perspiration, sebum and light without detrimentally modifying the fibres. The resistance to perspiration is particularly good. Furthermore, the dyeing process used makes it possible to induce a satisfactory "build-up" and/or strength of the colouring.

Other subjects, characteristics, aspects and advantages of the present invention will emerge even more clearly on reading the description and the examples that follow.

a) the ortho-diphenol(s)

In accordance with the present invention, the dyeing process uses a) one or more ortho-diphenols.

The ortho-diphenol(s) may be present in one or more cosmetic compositions used during the dyeing process.

The invention relates to one or more ortho-diphenols or mixtures of compounds comprising one or more aromatic rings, at least one of which is a benzene ring substituted with at least two hydroxyl (OH) groups borne by two adjacent carbon atoms of the said benzene group being present in the structure of the ortho-diphenol(s).

The aromatic ring is more particularly a fused aryl or fused heteroaromatic ring, i.e. optionally comprising one or more heteroatoms, such as benzene, naphthalene, tetrahydronaphthalene, indane, indene, anthracene, phenanthrene, indole, isoindole, indoline, isoindoline, benzofuran, dihydrobenzofuran, chroman, isochroman, chromene, isochromene, quinoline, tetrahydroquinoline and isoquinoline, the said aromatic ring comprising at least two hydroxyl groups borne by two adjacent carbon atoms of the aromatic ring. Preferentially, the aromatic ring of the ortho-diphenol derivatives according to the invention is a benzene ring.

The term "fused ring" means that at least two saturated or unsaturated and heterocyclic or non-heterocyclic rings have a shared bond, i.e. at least one ring is placed side-by-side with another ring.

The ortho-diphenols according to the invention may or may not be salified. They may also be in aglycone form (without attached sugar) or in the form of glycosylated compounds.

More particularly, the ortho-diphenol(s) a) represent a compound of formula (II), or an oligomer, tautomer, optical isomer or geometrical isomer thereof, and also a salt or solvate thereof, such as the hydrates:

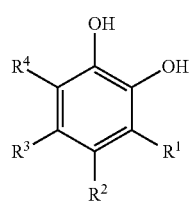

(II)

in which formula (II):

$R^1$ to $R^4$, which may be identical or different, represent: i) a hydrogen atom, ii) a halogen atom, or a group chosen from iii) hydroxyl, iv) carboxyl, v) ($C_1$-$C_{20}$) alkyl carboxylate or ($C_1$-$C_{20}$)alkoxycarbonyl, vi) optionally substituted amino, vii) optionally substituted linear or branched ($C_1$-$C_{20}$)alkyl, viii) optionally substituted linear or branched ($C_2$-$C_{20}$)alkenyl, ix) optionally substituted cycloalkyl, x) ($C_1$-$C_{20}$)alkoxy, xi) ($C_1$-$C_{20}$)alkoxy($C_1$-$C_{20}$)alkyl, xii) ($C_1$-$C_{20}$)alkoxyaryl, xiii) aryl which can optionally be substituted, xiv) aryl, xv) substituted aryl, xvi) heterocyclic which is saturated or unsaturated, optionally bearing a cationic or anionic charge and which is optionally substituted and/or optionally fused with an aromatic ring, preferably a benzene ring, the said aromatic ring optionally being substituted, in particular with one or more hydroxyl or glycosyloxy groups, xvii) a radical containing one or more silicon atoms; or two of the substituents borne by two adjacent carbon atoms $R^1$-$R^2$, $R^2$-$R^3$ or $R^3$-$R^4$ form, together with the carbon atoms bearing them, a saturated or unsaturated and aromatic or non-aromatic ring optionally containing one or more heteroatoms and optionally fused with one or more saturated or unsaturated rings optionally containing one or more heteroatoms. In particular, the compound of formula (II) comprises from one to four rings.

A particular embodiment of the invention relates to one or more ortho-diphenols of formula (II), two adjacent substituents $R^1$-$R^2$, $R^2$-$R^3$ or $R^3$-$R^4$ of which cannot form, with the carbon atoms that bear them, a pyrrolyl radical. According to a variant, $R^2$ and $R^3$ form a pyrrolyl or pyrrolidinyl radical fused to the benzene ring bearing the two hydroxyls.

For the purposes of the present invention, and unless otherwise indicated:

the saturated or unsaturated and optionally fused rings may also be optionally substituted;

the "alkyl" radicals are saturated, linear or branched, generally $C_1$-$C_{20}$, particularly $C_1$-$C_{10}$, hydrocarbon-based radicals, preferably $C_1$-$C_6$ alkyl radicals, such as methyl, ethyl, propyl, butyl, pentyl and hexyl;

the "alkenyl" radicals are unsaturated and linear or branched $C_2$-$C_{20}$ hydrocarbon-based radicals; preferably comprising at least one double bond, such as ethylene, propylene, butylene, pentylene, 2-methylpropylene and decylene;

the "aryl" radicals are monocyclic or fused or non-fused polycyclic carbon-based radicals preferentially comprising from 6 to 30 carbon atoms, at least one ring of which is aromatic; preferentially, the aryl radical is chosen from phenyl, biphenyl, naphthyl, indenyl, anthracenyl and tetrahydronaphthyl;

the "alkoxy" radicals are alkyl-oxy radicals with alkyl as defined previously, preferably $C_1$-$C_{10}$ alkyl, such as methoxy, ethoxy, propoxy and butoxy;

the "alkoxyalkyl" radicals are ($C_1$-$C_{20}$)alkoxy($C_1$-$C_{20}$) alkyl radicals, such as methoxymethyl, ethoxymethyl, methoxyethyl, ethoxyethyl, etc.;

the "cycloalkyl" radicals are $C_4$-$C_8$ cycloalkyl radicals, preferably cyclopentyl and cyclohexyl radicals; the cycloalkyl radicals may be substituted cycloalkyl radicals, in particular substituted with alkyl, alkoxy, carboxylic acid, hydroxyl, amine and ketone groups;

the "alkyl" or "alkenyl" radicals, when they are "optionally substituted", may be substituted with at least one atom or group borne by at least one carbon atom chosen from: i) halogen; ii) hydroxyl; iii) ($C_1$-$C_2$)alkoxy; iv)

($C_1$-$C_{10}$)alkoxycarbonyl; v) (poly)hydroxy($C_2$-$C_4$) alkoxy; vi) amino; vii) 5- or 6-membered heterocycloalkyl; viii) optionally cationic 5- or 6-membered heteroaryl, preferably imidazolium, optionally substituted with a ($C_1$-$C_4$)alkyl radical, preferably methyl; ix) amino substituted with one or two identical or different $C_1$-$C_6$ alkyl radicals optionally bearing at least: a) one hydroxyl group, b) one amino group optionally substituted with one or two optionally substituted ($C_1$-$C_3$) alkyl radicals, it being possible for the said alkyl radicals to form, with the nitrogen atom to which they are attached, a saturated or unsaturated and optionally substituted 5- to 7-membered heterocycle optionally comprising at least one other nitrogen or non-nitrogen heteroatom, c) a quaternary ammonium group —$N^+$R'R"R'", $M^-$ for which R', R" and R'", which may be identical or different, represent a hydrogen atom or a $C_1$-$C_4$ alkyl group; and $M^-$ represents the counterion of the corresponding organic acid, mineral acid or halide, d) or one optionally cationic 5- or 6-membered heteroaryl radical, preferentially imidazolium, optionally substituted with a ($C_1$-$C_4$)alkyl radical, preferably methyl; x) acylamino (—N(R)—C(O)—R') in which the R radical is a hydrogen atom or a ($C_1$-$C_4$)alkyl radical optionally bearing at least one hydroxyl group and the R' radical is a $C_1$-$C_2$ alkyl radical; a carbamoyl ((R)$_2$N—C(O)—) radical in which the R radicals, which may be identical or different, represent a hydrogen atom or a ($C_1$-$C_4$)alkyl radical optionally bearing at least one hydroxyl group; xi) alkylsulfonylamino (R'—S(O)$_2$—N(R)—) in which the R radical represents a hydrogen atom or a ($C_1$-$C_4$)alkyl radical optionally bearing at least one hydroxyl group and the R' radical represents a ($C_1$-$C_4$)alkyl radical, a phenyl radical; xii) aminosulfonyl ((R)$_2$N—S(O)$_2$—) in which the R radicals, which may be identical or different, represent a hydrogen atom or a ($C_1$-$C_4$)alkyl radical optionally bearing at least one group chosen from a) hydroxyl, b) carboxyl —C(O)—OH in the acid or salified form (preferably salified with an alkali metal or a substituted or unsubstituted ammonium); xiii) cyano; xiv) nitro; xv) carboxyl or glycosylcarbonyl; xvi) phenylcarbonyloxy optionally substituted with one or more hydroxyl groups; xvii) glycosyloxy; and phenyl group optionally substituted with one or more hydroxyl groups;

the "aryl" or "heterocyclic" radicals or the aryl or heterocyclic part of the radicals, when they are "optionally substituted", may be substituted with at least one atom or group borne by at least one carbon atom chosen from:
i) ($C_1$-$C_{10}$)alkyl, preferably $C_1$-$C_8$ alkyl, optionally substituted with one or more radicals chosen from the following radicals: hydroxyl, ($C_1$-$C_2$)alkoxy, (poly)hydroxy($C_2$-$C_4$)alkoxy, acylamino, amino substituted with two identical or different $C_1$-$C_4$ alkyl radicals optionally bearing at least one hydroxyl group or it being possible for the two radicals to form, with the nitrogen atom to which they are attached, a saturated or unsaturated and optionally substituted 5- to 7-membered, preferably 5- or 6-membered, heterocycle optionally comprising another nitrogen or non-nitrogen heteroatom; ii) halogen; iii) hydroxyl; iv) $C_1$-$C_2$ alkoxy; v) $C_1$-$C_{10}$ alkoxycarbonyl; vi) (poly)hydroxy($C_2$-$C_4$)alkoxy; vii) amino; viii) 5- or 6-membered heterocycloalkyl; ix) optionally cationic 5- or 6-membered heteroaryl, preferably imidazolium, optionally substituted with a ($C_1$-$C_4$)alkyl radical, preferably methyl; x) amino substituted with one or two identical or different $C_1$-$C_6$ alkyl radicals optionally bearing at least: a) one hydroxyl group, b) one amino group optionally substituted with one or two optionally substituted $C_1$-$C_3$ alkyl radicals, it being possible for the said alkyl radicals to form, with the nitrogen atom to which they are attached, a saturated or unsaturated and optionally substituted 5- to 7-membered heterocycle optionally comprising at least one other nitrogen or non-nitrogen heteroatom, c) one quaternary ammonium group —$N^+$R'R"R'", $M^-$ for which R', R" and R'", which may be identical or different, represent a hydrogen atom or a $C_1$-$C_4$ alkyl group; and $M^-$ represents the counterion of the corresponding organic acid, mineral acid or halide, d) one optionally cationic 5- or 6-membered heteroaryl radical, preferably imidazolium, optionally substituted with a ($C_1$-$C_4$)alkyl radical, preferably methyl; xi) acylamino (—N(R)—C(O)—R') in which the R radical is a hydrogen atom or a $C_1$-$C_4$ alkyl radical optionally bearing at least one hydroxyl group and the R' radical is a $C_1$-$C_2$ alkyl radical; xii) carbamoyl ((R)$_2$N—C(O)—) in which the R radicals, which may be identical or different, represent a hydrogen atom or a $C_1$-$C_4$ alkyl radical optionally bearing at least one hydroxyl group; xiii) alkylsulfonylamino (R'S(O)$_2$—N(R)—) in which the R radical represents a hydrogen atom or a $C_1$-$C_4$ alkyl radical optionally bearing at least one hydroxyl group and the R' radical represents a $C_1$-$C_4$ alkyl radical, a phenyl radical; xiv) aminosulfonyl ((R)$_2$N—S(O)$_2$—) in which the R radicals, which may be identical or different, represent a hydrogen atom or a $C_1$-$C_4$ alkyl radical optionally bearing at least one hydroxyl group; xv) carboxyl in the acid or salified form (preferably salified with an alkali metal or a substituted or unsubstituted ammonium); xvi) cyano; xvii) nitro; xviii) polyhaloalkyl, preferably trifluoromethyl; xix) a glycosylcarbonyl; xx) a phenylcarbonyloxy group optionally substituted with one or more hydroxyl groups; xxi) a glycosyloxy group; and xxii) a phenyl group optionally substituted with one or more hydroxyl groups;

for the purposes of the present invention, the term "glycosyl" radical means a radical derived from a mono- or polysaccharide;

the radicals "containing one or more silicon atoms" are preferably polydimethylsiloxane, polydiphenylsiloxane, polydimethylphenylsiloxane or stearoxy dimethicone radicals;

the "heterocyclic" radicals are radicals comprising, in at least one ring, one or more heteroatoms chosen in particular from O, N and S, preferably O or N, optionally substituted in particular with one or more alkyl, alkoxy, carboxyl, hydroxyl, amine or ketone groups. These rings may comprise one or more oxo groups on the carbon atoms of the heterocycle; mention may in particular be made, among the heterocyclic radicals that may be used, of furyl, pyranyl, pyrrolyl, imidazolyl, pyrazolyl, pyridyl or thienyl groups; even more preferably, the heterocyclic groups are fused groups, such as benzofuryl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, in particular with one or more OH groups.

The ortho-diphenol(s) that are useful in the process of the invention may be natural or synthetic. Among the natural ortho-diphenols are compounds that may be present in nature and that are reproduced by chemical (semi)synthesis.

The salts of the ortho-diphenols of the invention may be salts of acids or of bases. The acids may be mineral or organic. Preferably, the acid is hydrochloric acid, which results in chlorides.

The term "basifying agents" means that the bases as defined for d) may be mineral or organic. In particular, the bases are alkali metal hydroxides, such as sodium hydroxide, which results in sodium salts.

According to a particular embodiment of the invention, the composition comprises, as ingredient a), one or more synthetic ortho-diphenols that do not exist in nature.

According to another preferred embodiment of the invention, the composition that is useful in the process for dyeing keratin fibres comprises, as ingredient a), one or more natural ortho-diphenols.

More particularly, the ortho-diphenol(s) that may be used in the process of the invention according to a) are in particular:

flavanols such as catechin and epicatechin gallate,
flavonols such as quercetin,
anthocyanidins, for instance cyanidin, delphinidin and petunidin,
anthocyanins or anthocyans, for instance myrtillin,
ortho-hydroxybenzoates, for example gallic acid salts,
flavones, such as luteolin,
hydroxystilbenes, for example 3,3',4,5'-tetrahydroxystilbene, optionally oxylated (for example glucosylated),
3,4-dihydroxyphenylalanine and derivatives thereof,
2,3-dihydroxyphenylalanine and derivatives thereof,
4,5-dihydroxyphenylalanine and derivatives thereof,
dihydroxycinnamates, such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
quinones,
hydroxyxanthones,
1,2-dihydroxybenzene and derivatives thereof,
1,2,4-trihydroxybenzene and derivatives thereof,
1,2,3-trihydroxybenzene and derivatives thereof,
2,4,5-trihydroxytoluene and derivatives thereof,
proanthocyanidins and especially proanthocyanidins A1, A2, B1, B2, B3 and C1,
chroman and chromene compounds,
proathocyanins,
tannic acid,
ellagic acid,
and the mixtures of the preceding compounds.

According to the invention, the term "chromene or chroman" ortho-diphenol compounds means ortho-diphenols which comprise, in their structure, at least one bicycle of formula (A) below:

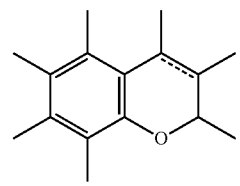

(A)

the endocyclic bond ---- representing a carbon-carbon single bond or else a carbon-carbon double bond, as illustrated by formula (A1) below, denoting the chromene family, and formula (A2) below, denoting the chroman family:

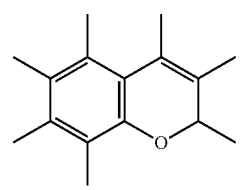

(A1)

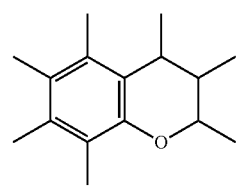

(A2)

More particularly, the ortho-diphenols of the invention are of formula (A) and are preferably chosen from the colourings of the following formulae:

formula (III), comprising, in its structure, the bicycle of formula (A2):

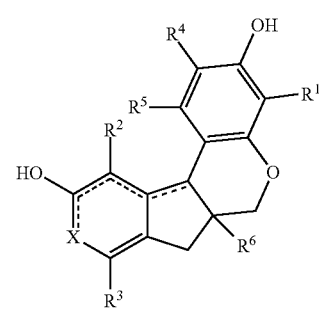

(III)

and also the tautomeric and/or mesomeric forms thereof, the stereoisomers thereof, the addition salts thereof with a cosmetically acceptable acid or base, and the hydrates thereof;

in which formula (III):

---- represents a carbon-carbon single bond or a carbon-carbon double bond, the sequence of these ---- bonds denoting two carbon-carbon single bonds and two carbon-carbon double bonds, the said bonds being conjugated, X represents a group:

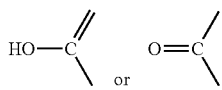

R¹, R², R³, R⁴, R⁵ and R⁶, which may be identical or different, represent a hydrogen atom, a hydroxyl group, an optionally substituted alkyl group, an optionally substituted alkoxy group or an optionally substituted acyloxy group; and)

formula (IV), comprising, in its structure, the bicycle of formula (A1):

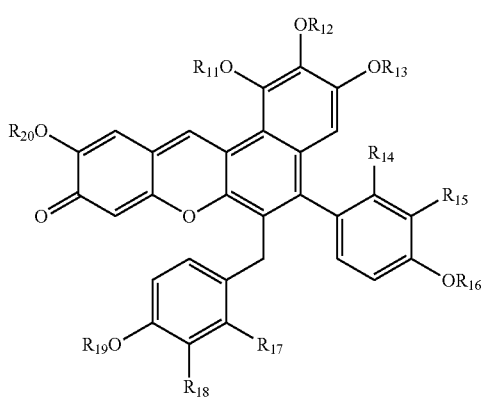

and also the tautomeric and/or mesomeric forms thereof, the stereoisomers thereof, the addition salts thereof with a cosmetically acceptable acid or base, and the hydrates thereof;

in which formula (IV):

$R_{11}$, $R_{12}$, $R_{13}$, $R_{16}$, $R_{19}$ and $R_{20}$, which may be identical or different, represent a hydrogen atom or a $C_1$-$C_4$ alkyl radical, and $R_{14}$, $R_{15}$, $R_{17}$ and $R_{18}$, which may be identical or different, represent a hydrogen atom, a hydroxyl radical or a $C_1$-$C_4$ alkoxy radical.

As regards the ortho-diphenols of formula (III) as defined above, they may be found in two tautomeric forms denoted (IIIa) and (IIIb):

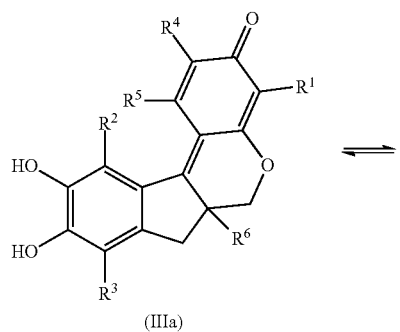

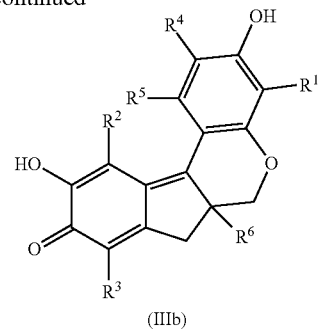

The alkyl radicals mentioned in the preceding definitions of the substituents are saturated and linear or branched hydrocarbon-based radicals, generally $C_1$-$C_{20}$, particularly $C_1$-$C_{10}$, preferably $C_1$-$C_6$, hydrocarbon-based radicals, such as methyl, ethyl, propyl, butyl, pentyl and hexyl.

The alkoxy radicals are alkyl-oxy radicals with the alkyl radicals as defined above and preferably the alkoxy radicals are $C_1$-$C_{10}$ alkoxy radicals, such as methoxy, ethoxy, propoxy and butoxy.

The alkyl or alkoxy radicals, when they are substituted, may be substituted with at least one substituent borne by at least one carbon atom chosen from: i) a halogen atom or ii) a hydroxyl group; iii) a $C_1$-$C_2$ alkoxy group; iv) a $C_1$-$C_{10}$ alkoxycarbonyl group; v) a (poly)hydroxy($C_2$-$C_4$)alkoxy group; vi) an amino group; vii) a 5- or 6-membered heterocycloalkyl group; viii) an optionally cationic 5- or 6-membered heteroaryl group, preferably imidazolium, optionally substituted with a ($C_1$-$C_4$)alkyl radical, preferably methyl; ix) an amino radical substituted with one or two identical or different $C_1$-$C_6$ alkyl radicals optionally bearing at least: a) one hydroxyl group, b) one amino group optionally substituted with one or two optionally substituted $C_1$-$C_3$ alkyl radicals, it being possible for the said alkyl radicals to form, with the nitrogen atom to which they are attached, a saturated or unsaturated and optionally substituted 5- to 7-membered heterocycle optionally comprising at least one other nitrogen or non-nitrogen heteroatom, c) one quaternary ammonium group —N⁺R'R''R''', M⁻ for which R', R'' and R''', which may be identical or different, represent a hydrogen atom or a $C_1$-$C_4$ alkyl group and M⁻ represents the counterion of the corresponding organic acid, mineral acid or halide, d) or one optionally cationic 5- or 6-membered heteroaryl radical, preferably imidazolium, optionally substituted with a ($C_1$-$C_4$)alkyl radical, preferably methyl; x) an acylamino (—NR—COR') radical in which the R radical is a hydrogen atom or a $C_1$-$C_4$ alkyl radical optionally bearing at least one hydroxyl group and the R' radical is a $C_1$-$C_2$ alkyl radical; xi) a carbamoyl ((R)₂N—CO—) radical in which the R radicals, which may be identical or different, represent a hydrogen atom or a $C_1$-$C_4$ alkyl radical optionally bearing at least one hydroxyl group; xii) an alkylsulfonylamino (R'SO₂—NR—) radical in which the R radical represents a hydrogen atom or a $C_1$-$C_4$ alkyl radical optionally bearing at least one hydroxyl group and the R' radical represents a $C_1$-$C_4$ alkyl radical, a phenyl radical; xiii) an aminosulfonyl ((R)₂N—SO₂—) radical in which the R radicals, which may be identical or different, represent a hydrogen atom or a $C_1$-$C_4$ alkyl radical optionally bearing at least one hydroxyl group; xiv) a carboxyl radical in the acid or salified form (preferably salified with an alkali metal or a substituted or unsubstituted ammonium); xv) a cyano group; xvi) a nitro group;

xvii) a carboxyl or glycosylcarbonyl group; xviii) a phenylcarbonyloxy group optionally substituted with one or more hydroxyl groups; xix) a glycosyloxy group; and xx) a phenyl group optionally substituted with one or more hydroxyl groups.

The term "glycosyl radical" means a radical derived from a monosaccharide or polysaccharide.

Preferably, the alkyl or alkoxy radicals of formula (III) are unsubstituted.

According to a particular embodiment of the invention, the dyes of formula (III) comprise a radical $R_6$ representing a hydroxyl group.

Another particular embodiment of the invention relates to the ortho-diphenols of formula (III) for which the radical $R_1$ represents a hydrogen atom or a hydroxyl group.

More particularly, the composition according to the invention may comprise one or more ortho-diphenols of formula (III) chosen from haematoxylin, haematein, brazilin and brazilein.

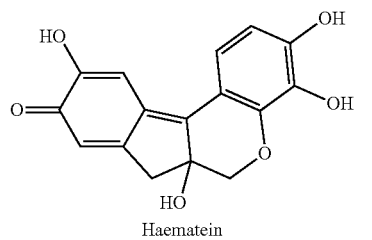
Haematein

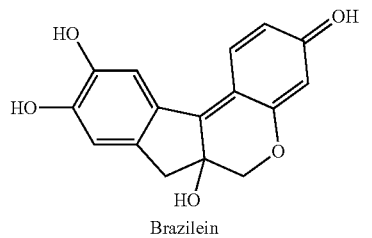
Brazilein

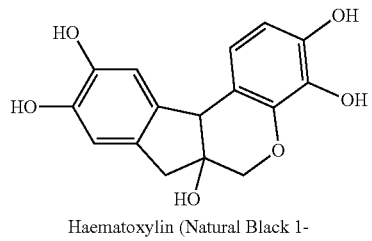
Haematoxylin (Natural Black 1-
CAS 517-28-2)

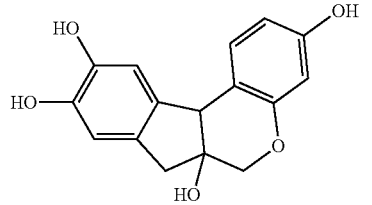
Brazilian (Natural Red 24-
CAS 474-07-7)

Brazilein is a conjugated form of a chroman compound of formula (A2). The tautomeric structures (IIIa) and (IIIb) illustrated above are found in the scheme below.

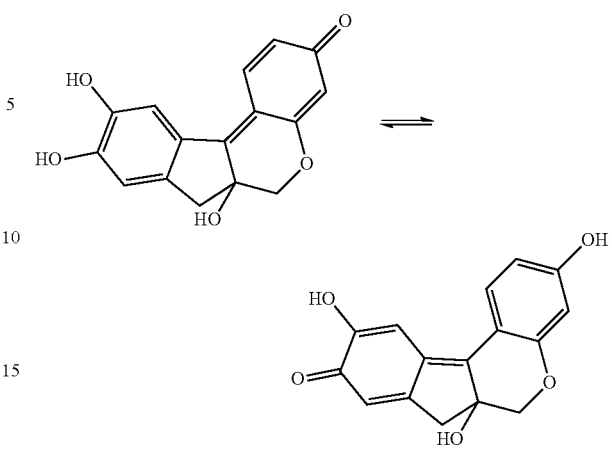

Brazilein

Among the ortho-diphenols of haematoxylin/haematein and brazilin/brazilein type, examples that may be mentioned include haematoxylin (Natural Black 1 according to the INCI name) and brazilin (Natural Red 24 according to the INCI name), dyes of the indochroman family, which are commercially available. The latter dyes may exist in an oxidized form and may be obtained synthetically or by extraction of plants or vegetables known to be rich in these dyes.

The ortho-diphenols of formula (III) may be used in the form of extracts. Use may be made of the following plant extracts (genus and species): *Haematoxylon campechianum, Haematoxylon brasiletto, Caesalpinia echinata, Caesalpinia sappan, Caesalpinia spinosa* and *Caesalpinia brasiliensis*.

The extracts are obtained by extracting the various plant parts, for instance the roots, the wood, the bark or the leaves.

According to a particular embodiment of the invention, natural ortho-diphenols of formula (I) are obtained from logwood, Pernambuco wood, sappan wood and Brazilwood.

As regards the ortho-diphenols of formula (IV), the ortho-diphenols used in the present invention are preferably those for which $R_{11}$ and $R_{13}$ represent an alkyl radical, preferably methyl.

Preferably, $R_{12}$, $R_{16}$, $R_{19}$ and $R_{20}$ denote, independently of each other, a hydrogen atom or an alkyl radical, preferably methyl.

Preferably, $R_{14}$ and $R_{17}$ denote, independently of each other, a hydrogen atom or an alkoxy radical, preferably methoxy.

Preferably, $R_{18}$ and $R_{15}$ denote, independently of each other, a hydrogen atom, a hydroxyl radical or an alkoxy radical, preferably methoxy.

A first particularly preferred family of ortho-diphenols that are suitable for use in the present invention is that of the dyes corresponding to formula (II) above for which $R_{12}$, $R_{15}$, $R_{16}$, $R_{17}$, $R_{19}$ and $R_{20}$ each represent a hydrogen atom. $R_{11}$ and $R_{13}$ each represent a methyl radical and $R_{14}$ represents a methoxy radical.

The preferred ortho-diphenols of this first family include those for which $R_{18}$ represents a methoxy radical (santalin B) or a hydroxyl radical (santalin A).

A second particularly preferred family of ortho-diphenols that are suitable for use in the present invention is that of the dyes corresponding to the formula (IV) above for which:
$R_{11}$ and $R_{13}$ each represent a methyl radical,
$R_{17}$ represents a methoxy radical.

A preferred dye of this second family is that for which, in addition, $R_{19}$ represents a methyl radical, $R_{20}$, $R_{12}$, $R_{14}$, $R_{18}$ and $R_{16}$ each represent a hydrogen atom and $R_{15}$ represents a hydroxyl radical (santarubin A).

A second preferred dye of this second family is that for which $R_{18}$, $R_{20}$, $R_{12}$, $R_{14}$ and $R_{16}$ represent a hydrogen atom, $R_{15}$ represents a methoxy radical and $R_{19}$ represents a methyl radical (santarubin B).

A third preferred family of ortho-diphenols of this second family is that for which $R_{20}$, $R_{12}$, $R_{14}$, $R_{15}$, $R_{16}$ and $R_{19}$ represent hydrogen and $R_{18}$ represents a hydroxyl radical (santarubin C).

Another preferred ortho-diphenol of this second family is that for which $R_{15}$ represents a methoxy radical, $R_{18}$ and $R_{14}$ represent a hydrogen atom and $R_{20}$, $R_{12}$, $R_{16}$ and $R_{19}$ represent a methyl radical (tetra-O-methylsantarubin).

The ortho-diphenols of formula (IV) can be used in the form of extracts. Use may be made of plant extracts of red woods, bringing together generally the species of red woods from Asia and West Africa of the genus *Pterocarpus* and of the genus *Baphia*. These woods are, for example, *Pterocarpus santalinus, Pterocarpus osun, Pterocarpus soyauxii, Pterocarpus erinaceus, Pterocarpus indicus* or *Baphia nitida*. These woods may also be called padauk, sandalwood, narra wood, camwood or bar wood.

Thus, extracts that may be used, comprising ortho-diphenols of formula (II), in the present invention may be obtained, for example, from red sandalwood (*Pterocarpus santalinus*) by aqueous basic extraction, such as the product sold under the trade name Santal Concentré SL 709C by the company COPIAA, or also by means of solvent extraction of sandalwood powder, such as the product sold under the trade name Santal Poudre SL PP by the same company COPIAA. Mention may also be made of the aqueous/alcoholic extract of powdered red sandalwood from the company Alban Muller.

Extracts that are also suitable for use in the present invention may be obtained from woods such as camwood *Baphia nitida* or also bar wood (*Pterocarpus soyauxii, Pterocarpus erinaceus*): the latter is thus split up and then ground: a conventional alcoholic extraction or one by percolation is subsequently performed on this ground material in order to collect a pulverulent extract that is particularly suitable for the implementation of the present invention.

The ortho-diphenol salts of formulae (III) and (IV) of the invention may be salts of acids or bases that are cosmetically acceptable.

The acids may be mineral or organic. Preferably, the acid is hydrochloric acid, which results in chlorides.

The bases may be mineral or organic. In particular, the bases are alkali metal hydroxides such as sodium hydroxide which leads to sodium salts.

Preferably, the ortho-diphenol(s) of formulae (III) and (IV) included in the composition according to the invention result from plant extracts. Use may also be made of mixtures of plant extracts.

The natural extracts of the ortho-diphenols according to the invention may be in the form of powders or liquids. Preferably, the extracts are in powder form.

In particular, the ortho-diphenols of the invention are chosen from catechin, quercetin, brazilin, haematein, haematoxylin, chlorogenic acid, caffeic acid, gallic acid, catechol, L-DOPA, pelargonidin, cyanidin, (−)-epicatechin, (−)-epigallocatechin, (−)-epigallocatechin 3-gallate (EGCG), (+)-catechin, isoquercetin, pomiferin, esculetin, 6,7-dihydroxy-3-(3-hydroxy-2,4-dimethoxyphenyl)coumarin, santalin AC, mangiferin, butein, maritimetin, sulfuretin, robtein, betanidin, pericampylinone A, theaflavin, proanthocyanidin A2, proanthocyanidin B2, proanthocyanidin C1, procyanidins DP 4-8, tannic acid, purpurogallin, 5,6-dihydroxy-2-methyl-1,4-naphthoquinone, alizarin, wedelolactone, variegatic acid, gomphidic acid, xerocomic acid and carnosol, and natural extracts containing them.

Preferably, the ortho-diphenols of the invention are chromenes or chromans and are chosen from haematein, haematoxylin, brazilein, brazilin and santalin A.

The term "carboxylate" is understood to mean carboxylic acid salt.

When the dye precursors have D and L forms, both forms may be used in the compositions according to the invention, as may the racemates.

According to one embodiment, the natural ortho-diphenols are derived from extracts of animals, bacteria, fungi, algae, plants and fruits, used in their entirety or partially. In particular regarding the plants, the extracts are derived from fruit, including citrus fruit, from vegetables, from trees and from shrubs. Mixtures of these extracts that are rich in ortho-diphenols as defined previously may also be used.

Preferably, the natural ortho-diphenol(s) of the invention are derived from extracts of plants or plant parts.

For the purposes of the invention, these extracts will be placed in the same category as compounds a).

The extracts are obtained by extraction of various plant parts, for instance the root, the wood, the bark, the leaf, the flower, the fruit, the seed, the pod or the peel.

Among the plant extracts, mention may be made of extracts of tea leaves and of rose.

Among the fruit extracts, mention may be made of extracts of apple, of grape (in particular of grape seed) or extracts of cocoa beans and/or pods.

Among the vegetable extracts, mention may be made of extracts of potato or of onion peel.

Among the extracts of tree wood, mention may be made of extracts of pine bark and extracts of campeachy wood.

Use may also be made of mixtures of plant extracts.

According to a particular embodiment of the invention, the ortho-diphenol derivative(s) are natural extracts, rich in ortho-diphenols. According to a preferred embodiment, the ortho-diphenol derivative(s) are solely natural extracts.

Preferentially, the ortho-diphenol(s) according to the invention are chosen from catechin, quercetin, haematein, haematoxylin, brazilin, brazilein, gallic acid and tannic acid, and natural extracts containing them chosen from grape marc, pine bark, green tea, onion, cocoa bean, logwood, redwood and gall nut.

More preferentially, the ortho-diphenol(s) of the invention are chosen from:
haematein, brazilein, gallic acid or tannic acid, when the dyeing process does not use a chemical oxidizing agent;
or else
haematoxylin, brazilin, gallic acid or tannic acid, when the dyeing process uses a chemical oxidizing agent.

The natural extracts according to the invention may be in the form of powders or liquids. Preferably, the extracts of the invention are in the form of powders.

According to the invention, the synthetic or natural ortho-diphenol(s) and/or the natural extract(s) used as ingredient a) in one or more cosmetic compositions that are useful in the process according to the invention preferably represent from 0.001% to 20% by weight of the total weight of the composition(s) comprising the ortho-diphenol(s) or the extract(s).

As regards the pure ortho-diphenols, the content in the composition(s) comprising them is preferably between 0.001% and 5% by weight of each of these compositions.

As regards the extracts, the content in the composition(s) containing the extracts per se is preferably between 0.5% and 20% by weight of each of these compositions.

b) the organic titanium salt(s):

According to a particular embodiment, the ingredient b) used in the composition and process of the invention is at least one titanium salt and b1) optionally at least one carboxylic acid of formula (I).

For the purposes of the present invention, the term "organic titanium salt" means the salts per se resulting from the action of at least one organic acid on Ti.

The term "organic acid" means an acid, i.e. a compound that is capable of releasing a cation or proton $H^+$ or $H_3O^+$, in aqueous medium, which comprises at least one optionally unsaturated, linear or branched $C_1$-$C_{20}$ hydrocarbon-based chain, or a (hetero)cycloalkyl or (hetero)aryl group and at least one acid chemical function chosen in particular from carboxyl COOH, sulfuric $SO_3H$, $SO_2H$, and phosphoric $PO_3H_2$, $PO_4H_2$. In particular, the organic acid(s) for forming the organic titanium salt(s) of the invention are chosen from the carboxylic acid(s) of formula (I) as defined previously and are preferably α-hydroxy acids such as lactic acid, glycolic acid, tartaric acid or citric acid.

Preferentially, the organic titanium salt derived from the action of one or more organic acids as defined previously, preferably carboxylic acids of formula (I) as defined previously, is an optionally charged (in particular negatively charged) complex, which is complexed with one or more carboxylate groups of carboxylic acids.

Preferentially, the organic titanium salt(s) of the invention are chosen from those of formula (V) below:

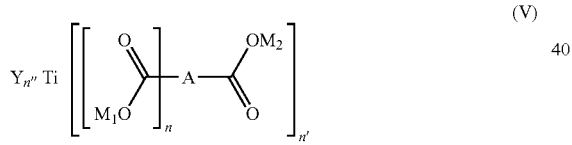

in which formula (V):

A is identical to that of formula (I)

n, n', n'' which may be identical or different, represent 1, 2, 3, 4 with n'+n''=6, $M_1$ and $M_2$, which may be identical or different, represent a cationic counterion such as a cation of an alkali metal (Na or K) or of an alkaline-earth metal (Ca) or an organic cation such as ammonium, preferably ammonium or a hydrogen atom;

$TiY_{n''}$, denoting $Ti(OH)_{n''}$, or $Ti(O)_{n''/2}$, or $Ti(OH)_{m1}(O)_{m2}$ with $m_1+m_2=n''$.

Preferentially, the radical A of compound (V) as defined previously represents a monovalent ($C_1$-$C_6$)alkyl or polyvalent ($C_1$-$C_6$)alkylene group optionally substituted with one or more hydroxyl groups, and n representing an integer between 0 and 5, such as between 0 and 2, inclusive; in particular, the carboxylic acid(s) used to form the organic titanium salt(s) of the invention are chosen from α-hydroxy acids; preferably, the acid is chosen from citric acid, lactic acid, tartaric acid and glycolic acid.

Preferentially, the organic titanium salt(s) of the invention are chosen from those of formula (V1) below:

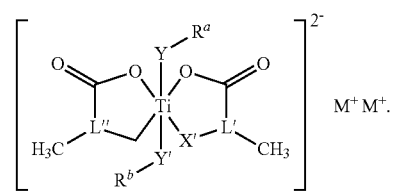

in which formula (V1):

L' and L'', which may be identical or different, represent a divalent (hetero)arylene, ($C_1$-$C_6$)alkylene or ($C_2$-$C_6$) alkenylene group, the said alkylene and arylene groups being optionally substituted with one or more atoms or groups chosen from halo, ($C_1$-$C_4$)alkyl, hydroxyl, thiol and (di)($C_1$-$C_4$)(alkyl)amino, carboxyl, and/or optionally interrupted with one or more heteroatoms such as oxygen;

preferably, L' and L'' are identical and represent a methylene or ethylene group optionally substituted with a ($C_1$-$C_4$)alkyl group;

X' and X'', which may be identical or different, represent a heteroatom such as oxygen, sulfur or amino $R^c$—N with $R^c$ representing a hydrogen atom or a ($C_1$-$C_4$)alkyl group; preferably, X' and X'' are identical and represent an oxygen atom;

Y and Y', which may be identical or different, are as defined for X' and X''; preferably, Y and Y' are identical and represent an oxygen atom;

$R^a$ and $R^b$, which may be identical or different, represent a hydrogen atom or a ($C_1$-$C_6$)alkyl, ($C_2$-$C_6$)alkenyl or (hetero)aryl group; particularly, $R^a$ and $R^b$, which are identical, represent a hydrogen atom or a ($C_1$-$C_4$)alkyl group, preferably hydrogen;

$M^+$, which may be identical or different, represents a cationic counterion such as a cation of an alkali metal (Na or K) or of an alkaline-earth metal (Ca) or an organic cation such as ammonium, preferably ammonium.

Preferably, the organic titanium salt(s) of the dyeing process are dihydroxybis(lactato)titanium(IV) salts such as those having the following formula:

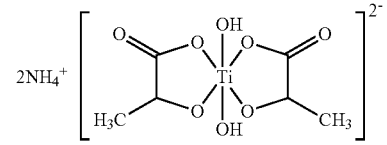

The dyeing process may use one or more organic acids b1) of formula (I) as defined previously.

According to an advantageous variant, the dyeing process also uses b1) one or more carboxylic acids of formula (I) as defined previously. More preferentially, the carboxylic acid(s) b1) are other than the carboxylic acids complexed to the Ti salts.

For example, if the carboxylic acid complexed to the titanium salt b) is lactic acid or the carboxylate salt thereof (lactate), the second acid b1) is other than lactic acid or lactate. Besides the organic Ti salt(s), the dyeing process of the invention may also use one or more additional Ti salts that are mineral. Preferably, the latter salts are applied to the keratin fibres in the same composition as that comprising at least one organic titanium salt b) as defined previously.

For the purposes of the present invention, the term "mineral titanium salt" means the salts per se derived from the action of a mineral acid on Ti.

The term "mineral acid" means an acid which does not comprise carbon atoms, apart from carbonic acid.

The mineral titanium salts are preferably chosen from titanium halides, titanium sulfates and titanium phosphates. Preferably, the titanium salts are mineral Ti(II), Ti(III) or Ti(IV) salts, more particularly Ti(III) or Ti(IV).

The organic titanium salt(s) are present in the cosmetic composition(s) used in the process according to the invention in a content ranging from 0.001% to 20% by weight, relative to the total weight of the composition(s) containing them.

Particularly, the organic titanium salt(s) and the mineral titanium salt(s) according to the invention are soluble in water in a proportion of at least 0.0001 g/l and better still at least 1 g/l.

c) Chemical Oxidizing Agent

According to a particular embodiment of the invention, the dyeing process also uses a chemical oxidizing agent. The term "chemical oxidizing agent" means an oxidizing agent other than atmospheric oxygen. More particularly, the dyeing process uses hydrogen peroxide a) urea peroxide; b) polymeric complexes that can release hydrogen peroxide, such as polyvinylpyrrolidone/$H_2O_2$, provided in particular in the form of powders, and the other polymeric complexes described in U.S. Pat. No. 5,008,093, U.S. Pat. No. 3,376,110 and U.S. Pat. No. 5,183,901; c) oxidases in the presence of an appropriate substrate (for example, glucose in the case of glucose oxidase or uric acid with uricase); d) metal peroxides which generate hydrogen peroxide in water, such as calcium peroxide or magnesium peroxide; e) perborates; or f) percarbonates.

According to a preferred embodiment of the invention, the composition comprises one or more chemical oxidizing agents chosen from a) urea peroxide; b) polymeric complexes which can release hydrogen peroxide chosen from polyvinylpyrrolidone/$H_2O_2$; c) oxidases; e) perborates and f) percarbonates.

In particular, the dyeing process uses hydrogen peroxide.

Moreover, the composition(s) comprising hydrogen peroxide or a hydrogen peroxide generating system may also include various adjuvants conventionally used in compositions for dyeing keratin fibres as defined below.

According to a particular embodiment of the invention, the chemical oxidizing agent(s) used preferably represent from 0.001% to 12% by weight of chemical oxidizing agents (of hydrogen peroxide) relative to the total weight of the composition(s) containing it or them, and even more preferentially from 0.2% to 2.7% by weight.

d) One or More Basifying Agents

According to a particular embodiment of the invention, the dyeing process uses one or more basifying agents. These are base(s) that can increase the pH of the composition(s) in which they are present. The basifying agent is a Bronsted, Lowry or Lewis base. It may be mineral or organic.

Particularly, the said agent is chosen from i) (bi)carbonates, ii) aqueous ammonia, iii) alkanolamines such as monoethanolamine, diethanolamine, triethanolamine and derivatives thereof, iv) oxyethylenated and/or oxypropylenated ethylenediamines, v) mineral or organic hydroxides, vi) alkali metal silicates such as sodium metasilicate, vii) amino acids, preferably basic amino acids such as arginine, lysine, ornithine, citrulline and histidine, and viii) the compounds of formula (VI) below:

in which formula (VI) W is a divalent ($C_1$-$C_8$)alkylene radical optionally substituted with at least one hydroxyl group or at least one ($C_1$-$C_4$)alkyl radical and/or optionally interrupted with at least one heteroatom, such as oxygen or sulfur, or by an —N($R_e$)— group; $R_a$, $R_b$, $R_c$, $R_d$ and $R_e$, which may be identical or different, represent a hydrogen atom or a ($C_1$-$C_4$)alkyl or hydroxy($C_1$-$C_4$)alkyl radical; preferably, W represents a propylene radical. The mineral or organic hydroxides are preferably chosen from a) hydroxides of an alkali metal, b) hydroxides of an alkaline-earth metal, for instance sodium hydroxide or potassium hydroxide, c) hydroxides of a transition metal, such as hydroxides of metals from groups III, IV, V and VI, d) hydroxides of lanthanides or actinides, quaternary ammonium hydroxides and guanidinium hydroxide.

The hydroxide may be formed in situ, for instance guanidine hydroxide, formed by reacting calcium hydroxide with guanidine carbonate.

The term "(bi)carbonates" i) is understood to mean:
a) carbonates of alkali metals ($Met_2^+$, $CO_3^{2-}$), of alkaline-earth metals ($Met'^{2+}$, $CO_3^{2-}$) of ammonium (($R''_4N^+$)$_2$,$CO_3^{2-}$) or of phosphonium (($R''_4P^+$)$_2$,$CO_3^{2-}$ with Met' representing an alkaline-earth metal and Met representing an alkali metal, and R", which may be identical or different, represent a hydrogen atom or an optionally substituted ($C_1$-$C_6$)alkyl group such as hydroxyethyl), and
b) bicarbonates, also known as hydrogen carbonates, of the following formulae:
R'$^+$, $HCO_3^-$, with R' representing a hydrogen atom, an alkali metal, an ammonium group $R''_4N^+$— or a phosphonium group $R''_4P^+$—, where R", which may be identical or different, represent a hydrogen atom or an optionally substituted ($C_1$-$C_6$)alkyl group, such as hydroxyethyl, and, when R' represents a hydrogen atom, the hydrogen carbonate is then known as dihydrogen carbonate ($CO_2$, $H_2O$); and)
$Met'^{2+}$ ($HCO_3^-$)$_2$, with Met' representing an alkaline-earth metal.

More particularly, the basifying agent is chosen from alkali metal or alkaline-earth metal (bi)carbonates and amino acids such as arginine; preferentially alkali metal (bi)carbonates and amino acids.

Mention may be made of Na, K, Mg and Ca carbonates or hydrogen carbonates and mixtures thereof, and in particular sodium hydrogen carbonate. These hydrogen carbonates may originate from a natural water, for example spring water from the Vichy basin or from La Roche Posay or Badoit water (cf. for example, patent FR 2 814 943). In particular, mention may be made of sodium carbonate [497-19-8]=$Na_2CO_3$, sodium hydrogen carbonate or sodium bicarbonate [144-55-8]=$NaHCO_3$, and sodium dihydrogen carbonate=$Na(HCO_3)_2$.

According to a particularly advantageous embodiment, the basifying agent(s) d) are chosen from amino acids, such as arginine, and (bi)carbonates, in particular alkali metal or alkaline-earth metal (bi)carbonates, alone or as mixtures. They are preferentially together during the dyeing process.

The basifying agent(s) as defined above preferably represent from 0.001% to 10% by weight of the weight of the composition(s) containing them, more particularly from 0.005% to 8% by weight of the composition.

Water:

According to one embodiment of the invention, water is preferably included in the process of the invention. It may originate from the moistening of the keratin fibres and/or from the composition(s) comprising compounds a) to d) as defined previously or from one or more other compositions.

Preferably, the water comes from at least one composition comprising at least one compound chosen from a) to d) as defined previously.

The Compositions:

The compositions according to the invention generally comprise water or a mixture of water and of one or more organic solvents or a mixture of organic solvents.

The term "organic solvent" means an organic substance that is capable of dissolving or dispersing another substance without chemically modifying it.

The Organic Solvents:

Examples of organic solvents that may be mentioned include $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether, diethylene glycol monomethyl ether, hexylene glycol, and also aromatic alcohols, such as benzyl alcohol or phenoxyethanol. Preferably, the dye composition, i.e. the composition comprising the ortho-diphenol(s) of the invention, comprises at least one organic solvent as defined previously and in particular an organic solvent chosen from aromatic alcohols, such as benzyl alcohol.

The organic solvents are present in proportions preferably of between 1% and 40% by weight approximately and even more preferentially between 5% and 30% by weight approximately, relative to the total weight of the dye composition.

The Adjuvants:

The composition(s) of the dyeing process in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

Carboxylic Acid b1):

According to one preferred embodiment of the invention, the dyeing process also use, in addition to compounds a), b) and optionally c), at least b1) one other particular carboxylic acid of formula (I) as defined previously. More particularly, the carboxylic acid(s) of formula (I) are such that A represents a monovalent ($C_1$-$C_6$)alkyl or polyvalent ($C_1$-$C_6$) alkylene group optionally substituted with one or more hydroxyl groups, and n represents an integer between 0 and 5, such as between 0 and 2, inclusive.

More particularly, the carboxylic acid(s) of the invention are chosen from the acids of formula (I) having a solubility in water of greater than or equal to 1% by weight at 25° C. and at atmospheric pressure.

Preferably, the acids of formula (I) comprise at least one hydroxyl group in their structure. Even more preferably, the acid is chosen from α-hydroxy acids. The preferred acids of the invention are chosen from glycolic acid, lactic acid, tartaric acid and citric acid.

The salts of the acids of formula (I) may be salts of organic or mineral bases, such as sodium hydroxide, aqueous ammonia or potassium hydroxide, or salts of organic amines, such as alkanolamines. The acids of formula (I) or salts thereof are present in the composition(s) containing them in a content ranging from 0.1% to 20% by weight.

The said adjuvants are preferably chosen from surfactants such as anionic or nonionic surfactants or mixtures thereof and mineral or organic thickeners.

The above adjuvants are generally present in an amount for each of them of between 0.01% and 40% by weight relative to the weight of the composition, and preferably between 0.1% and 20% by weight relative to the weight of the composition.

Needless to say, a person skilled in the art will take care to select this or these additional compound(s), if present, such that the advantageous properties intrinsically associated with the composition(s) that are useful in the dyeing process in accordance with the invention are not, or are not substantially, adversely affected by the envisioned addition(s).

The Additional Dyes:

The dyeing process using the ingredients a) to d) as previously defined may also use one or more additional direct dyes. These direct dyes are chosen, for example, from those conventionally used in direct dyeing, and among which mention may be made of any commonly used aromatic and/or non-aromatic dye such as neutral, acidic or cationic nitrobenzene direct dyes, neutral, acidic or cationic azo direct dyes, natural direct dyes other than ortho-diphenols, neutral, acidic or cationic quinone and in particular anthraquinone direct dyes, azine, triarylmethane, indoamine, methine, styryl, porphyrin, metalloporphyrin, phthalocyanine and methine cyanine direct dyes, and fluorescent dyes.

Mention may be made, among natural direct dyes, of lawsone, juglone, indigo, isatin, curcumin, spinulosin, apigenidin and orceins. Use may also be made of extracts or decoctions comprising these natural dyes and in particular henna-based poultices or extracts.

According to the invention, the direct dye(s) used in the composition(s) of the dyeing process according to the invention preferably represent from 0.001% to 10% by weight approximately of the total weight of the composition(s) and even more preferentially from 0.05% to 5% by weight approximately.

The composition according to the invention or the composition(s) of the process using the ingredients a) to d) as previously defined may also comprise one or more oxidation bases and/or one or more couplers conventionally used for dyeing keratin fibres.

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols, naphthalene-based couplers and heterocyclic couplers, and the addition salts thereof.

The oxidation base(s) present in the said composition(s) used in the process are generally each present in an amount of between 0.001% and 10% by weight of the total weight of the composition(s) containing them.

The cosmetic composition(s) of the invention may be in various galenical forms, such as a powder, a lotion, a mousse, a cream or a gel, or in any other form that is suitable for dyeing keratin fibres. They may also be packaged in a propellant-free pump-action bottle or under pressure in an aerosol container in the presence of a propellant and form a mousse.

pH of the Composition(s):

In accordance with the present invention, the pH of at least one of the cosmetic compositions comprising at least one of the ingredients a), b), b1) or c) is acidic, i.e. less than 7.0, particularly less than 5, more particularly at a pH of between 0 and 4 inclusive, preferably between 0.5 and 3.5, more preferably between 1 and 3.

According to one embodiment, the pH of the cosmetic composition(s) comprising one or more alkaline agents preferably chosen from (bi)carbonates is alkaline, i.e. greater than 7, preferably of between 8 and 12 and more particularly of between 8 and 10.5 inclusive.

Preferably, the composition containing the ortho-diphenol(s) a) has an acidic pH of less than 7, preferably less than 5, in particular a pH between 0 and 4 inclusive, preferably between 0.5 and 3.5, more preferably between 1 and 3.

According to a particular embodiment of the invention, the composition containing the mineral titanium or alkoxytitanium salt(s) b) and not containing (bi)carbonates has a pH of less than 7 and preferably of less than 5, in particular a pH between 0 and 4 inclusive, preferably between 0.5 and 3.5, more preferably between 1 and 3.

The pH of these compositions may be adjusted to the desired value by means of basifying agents as defined previously in d) or by using acidifying agents usually used in the dyeing of keratin fibres, or alternatively by means of standard buffer systems. Among the acidifying agents for the compositions used in the invention, examples that may be mentioned include mineral or organic acids, for instance hydrochloric acid, orthophosphoric acid, sulfuric acid, carboxylic acids, for instance acetic acid, tartaric acid, citric acid or lactic acid, or sulfonic acids.

The term "carboxylic acid" means a compound comprising at least one carboxylic acid —O(O)—OH group, preferably of formula (I) as defined previously, preferably comprising between 1 and 4 carboxylic acid groups, such as 1 or 2; or chosen from: i) $(C_1-C_{10})$alkyl-[C(O)—OH], and ii) het-[C(O)—OH]$_n$, with n an integer between 1 and 4, preferably between 1 and 2, inclusive, and het representing a heterocyclic group, such as pyrrolidone, it being possible for the alkyl or het group to be optionally substituted with one or more groups chosen in particular from OH and (di)$(C_1-C_6)$(alkyl)amino.

Dyeing Process in One or More Steps

The process for dyeing keratin fibres consists in treating, in one or more steps, with one or more cosmetic compositions containing the following ingredients, taken together or separately in the said composition(s):

a) one or more ortho-diphenols as defined previously;
b) one or more organic salts of titanium and b1) of carboxylic acid(s) of formula (I) as defined previously;
c) optionally, one or more chemical oxidizing agents chosen especially from hydrogen peroxide and one or more hydrogen peroxide generating systems;

it being understood that the composition or at least one of the compositions used in the dyeing process is at acidic pH, i.e. less than 7, preferably less than 5, in particular at a pH of between 0 and 4 inclusive, preferably between 0.5 and 3.5, more preferably between 1 and 3.

According to a particular embodiment of the invention, the dyeing process is performed in at least two steps which comprise a first step in which the keratin fibres are treated with a cosmetic composition comprising a) one or more ortho-diphenols as defined previously, b) one or more organic salts of titanium and of carboxylic acid(s) as defined previously and c) one or more carboxylic acids of formula (I) as defined previously; followed by a second step in which an alkaline cosmetic composition, i.e. a composition whose pH is greater than 7, preferably between 8 and 12 and in particular between 8 and 10.5, which comprises d) one or more basifying agents, is applied.

Preferentially, the cosmetic composition applied to the keratin fibres during the second step also comprises c) one or more chemical oxidizing agents chosen especially from hydrogen peroxide and one or more hydrogen peroxide generating systems, preferably hydrogen peroxide.

The leave-on time after application of the composition comprising the ortho-diphenol(s) is generally set at between 3 and 120 minutes, preferentially between 10 and 60 minutes and more preferentially between 15 and 45 minutes.

According to one particular embodiment of the invention, the process for dyeing keratin fibres is performed in two steps by applying to the keratin fibres a dye composition comprising the ingredients a), b), b1) and c) as defined previously and optionally one or more mineral titanium salts as defined previously, and then, in a second step, a composition comprising the ingredient d) and optionally the ingredient d) as defined previously is applied to the said keratin fibres, it being understood that at least one of the two compositions is aqueous. Preferably, the composition comprising the ortho-diphenol(s) is aqueous. Even more preferentially, the two compositions used in this embodiment are aqueous.

For this dyeing process, the leave-on time after application for the first step is generally set at between 3 and 120 minutes, preferentially between 10 and 60 minutes and more preferentially between 15 and 45 minutes. The application time of the composition comprising the ingredient e) during the second step is generally set at between 3 and 120 minutes, preferably between 3 and 60 minutes and more preferably between 5 and 30 minutes.

According to another embodiment, the process for dyeing keratin fibres is performed in two or three steps.

According to this embodiment, the process for dyeing keratin fibres is performed in one or more steps by applying to the keratin fibres, in a first stage, a cosmetic composition comprising:

a) one or more ortho-diphenol derivatives chosen especially from:
   haematein, brazilein, gallic acid or tannic acid, when the dyeing process does not use a chemical oxidizing agent d); or else
   haematoxylin or brazilin, when the dyeing process uses a chemical oxidizing agent d);
b) one or more organic titanium salts as defined previously, and
b1) optionally one or more carboxylic acids of formula (I) as defined previously with A representing a monovalent ($C_1$-$C_6$)alkyl or polyvalent ($C_1$-$C_6$)alkylene group optionally substituted with one or more hydroxyl groups, and n representing an integer between 0 and 5, such as between 0 and 2, inclusive; more particularly, the carboxylic acid or acids of the invention are chosen from citric acid, lactic acid, glycolic acid and tartaric acid;

then, in a second step, applying to the said fibres a cosmetic composition comprising:

c) optionally one or more chemical oxidizing agents chosen from hydrogen peroxide or one or more hydrogen peroxide generating systems;

d) one or more basifying agents chosen from alkanolamines and (bi)carbonates, in particular alkali metal or alkaline-earth metal (bi)carbonates, preferentially (bi)carbonates;

it being understood that:

the composition comprising the carboxylic acid(s) is at acidic pH, i.e. less than 7, preferably less than 5, in particular at a pH of between 1 and 3 inclusive; and the composition comprising the basifying agent(s) is at alkaline pH, preferably of between 8 and 12 and more particularly of between 8 and 10.

Irrespective of the application method, the application temperature is generally between room temperature (15° C. to 25° C.) and 220° C. and more particularly between 15° C. and 45° C. Thus, after application of the composition according to the invention, the head of hair may advantageously be subjected to a heat treatment by heating to a temperature of between 30° C. and 60° C. In practice, this operation may be performed using a styling hood, a hair-dryer, an infrared ray dispenser or other conventional heating appliances.

Use may be made, both as means for heating and for smoothing the head of hair, of a heating iron at a temperature of between 60° C. and 220° C. and preferably between 120° C. and 200° C.

Irrespective of the application method, it is possible to form rinsing or mechanical wiping and/or drying of the keratin fibres between each step, in particular before performing the final step comprising the application of a composition containing the ingredient e).

The steps of intermediate mechanical wiping and drying are also known as "controlled leave-in" to distinguish from "standard copious rinsing with water" and "leave-in". The term "mechanical wiping" of the fibres means rubbing an absorbent article on the fibres and the physical removal, by means of the absorbent article, of the excess ingredient(s) that have not penetrated into the fibres. The absorbent article may be a piece of fabric such as a towel, particularly a terry towel, a cloth or absorbent paper such as household roll towel.

According to a particularly advantageous process of the invention, the mechanical wiping is performed without total drying of the fibre, leaving the fibre moist.

The term "drying" means the action of evaporating the organic solvents and/or water present in one or more compositions used in the process of the invention, comprising or not comprising one or more ingredients a) to e) as defined previously. The drying may be performed with a source of heat (convection, conduction or radiation) by sending, for example, a stream of hot gas such as air necessary to evaporate the solvent(s). Sources of heat that may be mentioned include a hairdryer, a hairstyling hood, a hair-smoothing iron, an infrared ray dispenser or other standard heating appliances.

A particular form of the invention relates to a dyeing process which is performed at room temperature (25° C.).

In all the particular forms and variants of the processes previously described, the compositions mentioned are ready-to-use compositions that may result from the extemporaneous mixing of two or more compositions and in particular of compositions present in dyeing kits.

Dyeing Device or "Kit"

Another subject of the invention is a multi-compartment dyeing device or "kit". Advantageously, this kit comprises from 2 to 5 compartments comprising from 2 to 5 compositions in which are distributed the ingredients a) to d) as defined previously, which may be aqueous or pulverulent, with in particular at least one of the said compositions being aqueous.

According to a first variant, the kit comprises five compartments, the first four compartments respectively comprising the powdered ingredients a), b), c) and d) as defined previously and the fifth compartment containing an aqueous oxidizing composition, such as water comprising d) as defined previously.

In this other embodiment, at least one of the four compositions is aqueous and the ortho-diphenol derivative(s) may be in powder form.

In another kit variant, this kit comprises two compartments, in which the first composition contained in the first compartment comprises a), b) and c) and the second compartment comprises d) in powder form or in aqueous medium; preferably, the second composition is aqueous.

In another kit variant, this kit comprises three compartments, in which the first composition contained in the first compartment comprises a) and b) and the second compartment comprises d) in powder form or in aqueous medium; preferably, the second composition is aqueous and the third compartment comprises c).

According to one variant, the device according to the invention also comprises an additional composition comprising one or more treating agents.

The compositions of the device according to the invention are packaged in separate compartments, optionally accompanied by suitable application means which may be identical or different, such as fine brushes, coarse brushes or sponges.

The device mentioned above may also be equipped with a means for dispensing the desired mixture on the hair, for instance the devices described in patent FR 2 586 913.

A subject of the invention is also the use of said cosmetic dye composition for dyeing keratin fibres.

Another subject of the invention is the use of one or more carboxylic acids of formula (I) as defined previously for improving the dyeing of keratin fibres performed using ortho-diphenol(s) in the presence of organic titanium salt(s).

For the purposes of the present invention, the term "buildup" of the colour of the keratin fibres means the variation in colouring between locks of undyed grey hair and locks of dyed hair.

The example that follows serves to illustrate the invention without, however, being limiting in nature.

EXAMPLES OF DYEING

Example 1

The following compositions are prepared from the following ingredients in the following proportions, indicated in grams:

Dying Compositions:

| Ingredients | CAS | Composition 1 | Composition 2 | Composition 3 |
|---|---|---|---|---|
| Pure haematoxylin | 517-28-2 | 4 g | 4 g | 4 g |
| Ethanol | | 15 g | 15 g | 15 g |
| Lactic acid | | 18.1 | 10.1 | 9.9 |
| Dihydroxybis(ammonium lactato)titanium(IV) at 50% by weight (ref. 388165 from Aldrich) | 65104-06-5 | 15.7 | 12.1 | 12.1 |
| Titanium(III) sulfate at 45% by weight (ref. 495182 from Aldrich) | 19495-50-8 | — | — | 2.44 |
| Water | | qs 100 g | qs 100 g | qs 100 g |
| pH | | 2.6 | 2.4 | 2 |

Alkaline Composition B:

| Ingredients | Amount |
|---|---|
| Sodium bicarbonate | 5 g |
| L-Arginine | 7 g |
| Aqueous hydrogen peroxide solution (50%) | 1.7 g |
| Water | qs 100 g |
| pH agent | pH 9.2 |

Procedure

Each composition 1, 2 or 3 is applied to locks of natural or permanent-waved Caucasian hair comprising 90% white hairs and locks of natural Chinese hair comprising 100% white hairs, in a proportion of 2 grams of composition per 1 gram of hair. The compositions are subsequently left to stand on the locks for 45 minutes at a temperature of 40° C.

Composition B is subsequently applied to each of the locks in a proportion of 2 grams of composition per one gram of locks. The pH of composition B is 9.2. The leave-in time is 15 minutes at a temperature of 45° C. The locks are subsequently washed with Elvive multivitamin shampoo, rinsed and then dried under a hood.

The colourings obtained are measured using a Minolta CM-3600D spectrocolorimeter in comparison with undyed hair.

The persistences are also measured using the same spectrocolorimeter in comparison with hair that has not undergone a persistence test.

Dyeing Results

The colour of the locks was evaluated in the CIE $L^* a^* b^*$ system using a Minolta Spectrophotometer CM3600D colorimeter. In this $L^* a^* b^*$ system, the three parameters denote, respectively, the colour intensity ($L^*$), the green/red colour axis ($a^*$) and the blue/yellow colour axis ($b^*$).

Buildup* of the Colour:

The variation in colouring between the locks of permanent-waved grey hair comprising 90% white hairs (90 PW) or the locks comprising 100% white hairs which are untreated (control) and after treatment or dyeing are defined by ($\Delta E^*$) according to the following equation:

$$\Delta E^* = \sqrt{(L^*-L_o^*)^2+(a^*-a_o^*)^2+(b^*-b_o^*)^2}$$

In this equation, $L^*$, $a^*$ and $b^*$ represent the values measured on locks of hair after dyeing and $L_o^*$, $a_o^*$ and $b_o^*$ represent the values measured on locks of undyed virgin hair. The higher the $\Delta E^*$ value, the better the colour buildup.
* or also called colour uptake

| Untreated hair | $L^*$ | $a^*$ | $b^*$ |
|---|---|---|---|
| Natural Caucasian, 90% white hairs | 68.76 | 0.72 | 15.5 |
| Permanent-waved Caucasian, 90% white hairs | 67.38 | 0.76 | 15.03 |
| Natural Chinese, 100% white hairs | 74.92 | 2.4 | 23.92 |

Black locks are obtained which are very intensely coloured, as shown by the following colorimetric measurements

| Treated hair | Colour | $L^*$ | $a^*$ | $b^*$ | $\Delta E^*$ buildup |
|---|---|---|---|---|---|
| Composition 1 + B | | | | | |
| Natural Caucasian, 90% white hairs | Black | 25.61 | 1.07 | −0.07 | 44.37 |
| Permanent-waved Caucasian, 90% white hairs | Black | 22.36 | −0.03 | −0.11 | 43.36 |
| Natural Chinese, 100% white hairs | Grey/black | 26.81 | 0.87 | −0.57 | 55.47 |
| Composition 2 + B | | | | | |
| Natural Caucasian, 90% white hairs | Black | 23.21 | 1.51 | −0.02 | 46.59 |
| Permanent-waved Caucasian, 90% white hairs | Black | 21.92 | 0.01 | −0.1 | 43.78 |
| Natural Chinese, 100% white hairs | Black | 23.59 | 1.21 | −0.23 | 58.23 |
| Composition 3 + B | | | | | |
| Natural Caucasian, 90% white hairs | Black | 22.3 | 0.31 | −0.6 | 47.65 |
| Permanent-waved Caucasian, 90% white hairs | Black | 22.59 | −0.01 | 0.29 | 43.02 |
| Natural Chinese, 100% white hairs | Black | 24.66 | −0.37 | 0.49 | 57.01 |

Persistence of the Colour

The hair treated with composition 3+B is then subjected to tests of persistence towards light (Xenotest alpha).

The hair dyed with the composition (3+B) is also subjected to tests of persistence:
  towards sweat by immersion at 37° C. in an oven for 48 hours in artificial sweat of composition C.

| Ingredients | Amount |
|---|---|
| Sodium chloride | 10 g |
| Disodium phosphate | 1 g |
| Histidine | 0.25 g |
| Water | qs 100 g |
| Lactic acid | qs pH 3.2 |

The locks dyed using the compositions described above were exposed to light.

The colour of the locks was evaluated, before and after exposure to light, before and after treatment with sweat or before and after successive shampooing operations, in the $L^* a^* b^*$ system, by means of a spectrophotometer as defined above.

The variation in the colouring of the locks, before and after exposure to light, before and after treatment with sweat or before and after successive shampooing operations, is measured by ($\Delta E'$) according to the following equation:

$$\Delta E' = \sqrt{(L'^*-L_o^*)^2+(a'^*-a_o^*)^2+(b'^*-b_o^*)^2}$$

In this equation, L'*, a'* and b'* represent the values measured after external treatment of the locks (exposure to light, sweat or successive shampooing operations) and $L_0^*$, $a_0^*$ and $b_0^*$ represent the values measured before exposure.

The greater the ΔE' value, the greater the difference in colour of the lock before and after external treatment, which shows a reduced persistence towards light.

The results in terms of persistence are collated in the following table:

| Hair | Light exposure (40 h Xenotest) % loss/ unexposed hair | Artificial sweat (48 h, 37° C.) % loss/ unexposed hair |
|---|---|---|
| Compositions 3 + B | | |
| Natural Caucasian, 90% white hairs | — | — |
| Permanent-waved Caucasian, 90% white hairs | — | 4.03 |
| Natural Chinese, 100% white hairs | 5.31 | — |

It is seen that the hair dyed according to the invention shows a very good level of persistence which is confirmed by the colorimetric values (very low percentages of losses in ΔE' when compared with hair that has not undergone the persistence test).

Example 2

The following compositions are prepared from the following ingredients in the following proportions, indicated in grams:

Dye Composition 4:

| Ingredients | CAS | Amount |
|---|---|---|
| Pure haematoxylin | 517-28-2 | 4 g |
| Ethanol | | 15 g |
| Lactic acid | | 18 |
| Dihydroxybis(ammonium lactato)titanium(IV) at 50% by weight (ref. 388165 from Aldrich) | 65104-06-5 | 16 |
| Water | | qs 100 g |
| pH | | 2.6 |

Revealing Composition D:

| Ingredients | Code | Amount |
|---|---|---|
| Sodium bicarbonate | 67 | 5 g |
| L-Arginine | 52298 | 7 g |
| Aqueous hydrogen peroxide solution (50%) | 1618 | 2.4 g |
| Water | 511 S | qs 100 g |
| pH agent | | pH 9.2 |

Locks of natural and permanent-waved Caucasian hair containing 90% white hairs and natural Chinese hair containing 100% white hairs are successively treated with:
  composition 4, which is left to stand on the locks for 45 minutes at 40° C. and the locks are then manually dried,
  composition B, which is then left to stand on the locks for 15 minutes at 40° C.

On conclusion of these leave-in times, the locks are washed with Elvive multivitamin shampoo, rinsed and then dried under a hood.

The colourings obtained are measured using a Minolta CM-3600D spectrocolorimeter in comparison with undyed hair. The persistences are also measured using the same spectrocolorimeter in comparison with hair that has not undergone a persistence test.

Buildup of the Colour:

Black locks are obtained which are very intensely coloured, as shown by the colorimetric measurements

| Hair | Colour | L* | a* | b* | ΔE* buildup |
|---|---|---|---|---|---|
| Composition 4 + B | | | | | |
| Natural Caucasian, 90% white hairs | Black | 20.66 | 1.28 | 0.92 | 50.26 |
| Natural permanent-waved Caucasian, 90% white hairs | Black | 22.5 | 0.91 | 1.49 | 46.88 |
| Natural Chinese, 100% white hairs | Grey/ black | 28.08 | 1.64 | 2.79 | 51.39 |

The hair dyed with the composition (4+D) is also subjected to a test of persistence towards light (Xenotest lambda).

Persistence Results

The results in terms of persistence are collated in the following table:

| Hair | Light exposure (40 h Xenotest) % loss/ unexposed hair |
|---|---|
| Composition 4 + D | |
| Natural Caucasian, 90% white hairs | 2.63 |
| Natural permanent-waved Caucasian, 90% white hairs | 3.86 |
| Natural Chinese, 100% white hairs | 14.15 |

It is seen that the hair dyed according to the invention shows a very good level of persistence which is confirmed by the colorimetric values (very low percentages of losses in ΔE' when compared with hair that has not undergone any test).

The invention claimed is:

1. A method for dyeing keratinous fibers, the method comprising:
  applying to the fibers:
  a) a first composition comprising at least one ortho-diphenol;
  b) a second composition comprising at least one organic titanium salt of oxidation state 3 or Ti(III), or 4 or Ti(IV);
  c) a third composition comprising at least one carboxylic acid chosen from those of formula (I) below, or salts thereof:

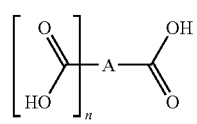

(I)

wherein:
  A is chosen from a monovalent group when n is zero or a polyvalent group when n is greater than or equal to 1; a saturated or unsaturated, cyclic or non-cyclic, and aromatic or non-aromatic hydrocarbon-based group comprising from 1 to 50 carbon atoms which is optionally interrupted with at least one heteroatom and/or optionally substituted; or a monovalent ($C_1$-

$C_6$)alkyl group; or a polyvalent ($C_1$-$C_6$)alkylene group optionally substituted with at least one hydroxyl group; and n is an integer ranging from 0 to 10; and d) optionally, a fourth composition comprising at least one chemical oxidizing agent chosen from hydrogen peroxide, urea peroxide, or at least one hydrogen peroxide generating system;

wherein the first composition, the second composition, the third composition, and/or the fourth composition are optionally identical; and wherein at least one composition chosen from the first composition, the second composition, the third composition, or the fourth composition has an acidic pH.

2. The method according to claim 1, wherein the at least one ortho-diphenol comprises an aromatic ring chosen from benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline, or isoquinoline, wherein the aromatic ring comprises at least two hydroxyl groups borne by two contiguous adjacent atoms of the aromatic ring.

3. The method according to claim 1, wherein the at least one ortho-diphenol is chosen from those of formula (II) below, or oligomers, tautomers, optical isomers, geometrical isomers, salts, solvates, or hydrates thereof:

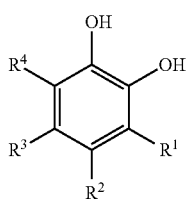

(II)

wherein:

$R^1$ to $R^4$, which may be identical or different, are chosen from: i) hydrogen, ii) halogen atoms, iii) hydroxyl groups, iv) carboxyl groups, v) ($C_1$-$C_{20}$) alkyl carboxylate or ($C_1$-$C_{20}$)alkoxycarbonyl groups, vi) optionally substituted amino groups, vii) optionally substituted linear or branched ($C_1$-$C_{20}$)alkyl groups, viii) optionally substituted linear or branched ($C_2$-$C_{20}$)alkenyl groups, ix) optionally substituted cycloalkyl groups, x) ($C_1$-$C_{20}$)alkoxy groups, xi) ($C_1$-$C_{20}$)alkoxy($C_1$-$C_{20}$)alkyl groups, xii) ($C_1$-$C_{20}$) alkoxyaryl groups, xiii) aryl groups which can optionally be substituted, xiv) aryl groups, xv) substituted aryl groups, xvi) heterocyclic groups which are saturated or unsaturated, optionally bearing a cationic or anionic charge and which are optionally substituted and/or optionally fused with an aromatic ring, the aromatic ring optionally substituted, or xvii) radical groups containing at least one silicon atom; or, optionally:

two of the substituents borne by two adjacent carbon atoms $R^1$-$R^2$, $R^2$-$R^3$, or $R^3$-$R^4$ optionally form, together with the carbon atoms bearing them, a saturated or unsaturated, aromatic or non-aromatic ring optionally containing at least one heteroatom and optionally fused with at least one saturated or unsaturated ring optionally containing at least one heteroatom; or $R^1$ to $R^4$ together form from one to four rings; or $R^2$ and $R^3$ form a pyrrolyl or pyrrolidinyl radical fused to the benzene ring bearing the two hydroxyls.

4. The method according to claim 1, wherein the at least one ortho-diphenol is chosen from:

flavanols, catechin, epicatechin gallate, or quercetin;
anthocyanidins, cyanidin, delphinidin, or petunidin;
anthocyanins, anthocyans, or myrtillin;
ortho-hydroxybenzoates or gallic acid salts;
flavones or luteolin;
hydroxystilbenes, or 3,3',4,5'-tetrahydroxystilbene, optionally oxylated or gluocosylated;
3,4-dihydroxyphenylalanine or derivatives thereof;
2,3-dihydroxyphenylalanine or derivatives thereof;
4,5-dihydroxyphenylalanine or derivatives thereof;
dihydroxycinnamates, caffeic acid, or chlorogenic acid;
ortho-polyhydroxycoumarins;
ortho-polyhydroxyisocoumarins;
ortho-polyhydroxycoumarones;
ortho-polyhydroxyisocoumarones;
ortho-polyhydroxychalcones;
ortho-polyhydroxychromones;
quinones;
hydroxyxanthones;
1,2-dihydroxybenzene or derivatives thereof;
1,2,4-trihydroxybenzene or derivatives thereof;
1,2,3-trihydroxybenzene or derivatives thereof;
2,4,5-trihydroxytoluene or derivatives thereof;
proanthocyanidins, proanthocyanidins A1, A2, B1, B2, B3, or C1;
chromans or chromenes;
proathocyanins;
tannic acid;
ellagic acid;
haematein;
brazilein;
gallic acid;
haematoxylin;
brazilin; or
mixtures thereof.

5. The method according to claim 1, wherein the at least one ortho-diphenol is chosen from extracts of animals, bacteria, fungi, algae, plants, or fruit.

6. The method according to claim 1, wherein the at least one carboxylic acid is chosen from compounds of formula (I) wherein A is chosen from a monovalent ($C_1$-$C_6$)alkyl or polyvalent ($C_1$-$C_6$)alkylene group optionally substituted with at least one hydroxyl groups, and n is an integer ranging from 0 to 5; α-hydroxy acids; citric acid; lactic acid; tartaric acid; or glycolic acid.

7. The method according to claim 1, wherein the at least one carboxylic acid is present in an amount ranging from about 0.1% to about 20% by weight, relative to the total weight of the composition.

8. The method according to claim 1, wherein the at least one organic titanium salt is derived from the reaction of at least one organic acid with titanium, wherein the at least one organic acid is chosen from organic acids comprising:

a) at least one optionally unsaturated, linear or branched $C_1$-$C_{20}$ hydrocarbon-based chain, or a (hetero)cycloalkyl or (hetero)aryl group; and b) at least one acid chemical function chosen from carboxyl COOH, sulfuric $SO_3H$, $SO_2H$, or phosphoric $PO_3H_2$, $PO_4H_2$.

9. The method according to claim 8,
wherein the at least one organic acid is represented by formula (I), and
wherein the at least one organic acid is different from the at least one carboxylic acid.

10. The method according to claim 8, wherein the titanium of the organic titanium salt has an oxidation state of 4 or Ti(IV).

11. The method according to claim 1, wherein the at least one organic titanium salt is chosen from those of formula (V) below:

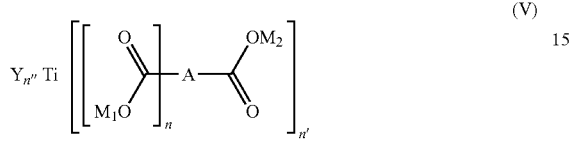

wherein:
A is chosen from a monovalent group when n is zero or a polyvalent group when n is greater than or equal to 1; a saturated or unsaturated, cyclic or non-cyclic, and aromatic or non-aromatic hydrocarbon-based group comprising from 1 to 50 carbon atoms which is optionally interrupted with at least one heteroatom and/or optionally substituted; a monovalent ($C_1$-$C_6$) alkyl group; or a polyvalent ($C_1$-$C_6$)alkylene group optionally substituted with at least one hydroxyl group;
n, n', and n", which may be identical or different, are chosen from 1, 2, 3, or 4, wherein n'+n"=6;
$M_1$ and $M_2$, which may be identical or different, are chosen from a cationic counterion, a cation of an alkali metal, Na, K, a cation of an alkaline-earth metal, Ca, an organic cation, or ammonium; and
$TiY_{n''}$ is chosen from $Ti(OH)_{n''}$, $Ti(O)_{n''/2}$, or $Ti(OH)_{m_1}(O)_{m_2}$ with $m_1+m_2=n''$.

12. The method according to claim 11, wherein the at least one organic titanium salt is chosen from dihydroxybis (lactato)titanium(IV) salts, or those represented by the formula below:

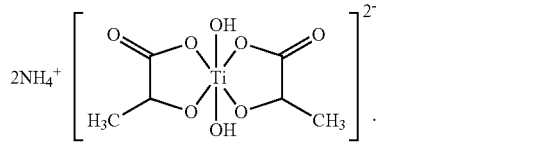

13. The method according to claim 1, wherein the second composition further comprises at least one mineral titanium salt, titanium halide, titanium sulfate, or titanium phosphate.

14. The method according to claim 1, further comprising applying a fourth composition comprising at least one chemical oxidizing agent chosen from hydrogen peroxide, urea peroxide, or at least one hydrogen peroxide generating system.

15. The method according to claim 1, further comprising applying at least one basifying agent chosen from i) carbonates or bicarbonates; ii) aqueous ammonia; iii) alkanolamines, monoethanolamine, diethanolamine, triethanolamine, or derivatives thereof; iv) oxyethylenated and/or oxypropylenated ethylenediamines; v) mineral or organic hydroxides; vi) alkali metal silicates or sodium metasilicates; vii) amino acids, basic amino acids, arginine, lysine, ornithine, citrulline or histidine; viii) the compounds of formula (V) below:

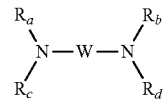

wherein:
W is chosen from a divalent ($C_1$-$C_8$)alkylene radical optionally substituted with at least one hydroxyl group, or at least one ($C_1$-$C_4$)alkyl radical optionally interrupted with at least one heteroatom, oxygen, or sulfur, or —N($R_e$)— group; and
$R_a$, $R_b$, $R_c$, $R_d$ and $R_e$, which may be identical or different, are chosen from a hydrogen atom, ($C_1$-$C_4$) alkyl radicals, hydroxy($C_1$-$C_4$)alkyl radicals, propylene radicals, or mixtures thereof.

16. The method according to claim 1, wherein the at least one of the first composition, the second composition, the third composition, and/or the fourth composition further comprise at least one organic solvent chosen from lower $C_1$-$C_4$ alkanols, ethanol, isopropanol, polyols, polyol ethers, 2-butoxyethanol, propylene glycol, propylene glycol monomethyl ether, diethylene glycol monoethyl ether, diethylene glycol monomethyl ether, hexylene glycol, aromatic alcohols, benzyl alcohol, phenoxyethanol, or mixtures thereof.

17. The method according to claim 1, comprising:
applying to the keratin fibers the first composition, the second composition, and the third composition to form treated keratin fibers; and
applying to the treated keratin fibers an alkaline composition comprising:
at least one basifying agent, and
optionally at least one chemical oxidizing agent chosen from hydrogen peroxide, urea peroxide, or at least one hydrogen peroxide generating system.

18. The method according to claim 17, wherein:
the at least one ortho-diphenol is chosen from haematein, brazilein, gallic acid or tannic acid, when the method does not comprise applying the at least one chemical oxidizing agent; or haematoxylin or brazilin, when the method does comprise applying the at least one chemical oxidizing agent;
the at least one organic titanium salt is chosen from Ti(IV) salts or complexes; optionally in the presence of at least one mineral titanium salt; and
the at least one basifying agent is chosen from alkanolamines, carbonates, bicarbonates, alkali metal carbonates, alkali metal bicarbonates, alkaline earth metal carbonates, or alkaline earth metal bicarbonates;
the third composition comprising the at least one carboxylic acid has an acidic pH; and
the composition comprising the at least one basifying agent has an alkaline pH.

19. A cosmetic composition for dyeing keratinous fibers, comprising:
a) at least one ortho-diphenol;
b) at least one organic titanium salt of oxidation state 3 or Ti(III), or 4 or Ti(IV);
c) at least one carboxylic acid chosen those of formula (I) below, or salts thereof:

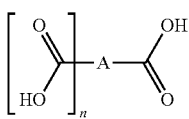

(I)

wherein:
- A is chosen from a monovalent group when n is zero or a polyvalent group when n is greater than or equal to 1, saturated or unsaturated, cyclic or non-cyclic, and aromatic or non-aromatic hydrocarbon-based group comprising from 1 to 50 carbon atoms which is optionally interrupted with at least one heteroatom and/or optionally substituted, or a monovalent ($C_1$-$C_6$)alkyl group; or a polyvalent ($C_1$-$C_6$)alkylene group optionally substituted with at least one hydroxyl group;
- n is an integer ranging from 0 to 10;
- d) optionally, at least one chemical oxidizing agent chosen from hydrogen peroxide, urea peroxide, or at least one hydrogen peroxide generating system; wherein the composition has an acidic pH; and
- e) at least one basifying agent chosen from alkanolamines, carbonates, or bicarbonates.

20. A multi-compartment device comprising from 2 to 5 compartments containing from 2 to 5 compositions, the device comprising:
- a) a first composition comprising at least one ortho-diphenol;
- b) a second composition comprising at least one organic titanium salt of oxidation state 3 or Ti(III), or 4 or Ti(IV);
- c) a third composition comprising at least one carboxylic acid chosen from those of formula (I) below, or salts thereof:

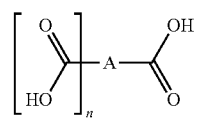

(I)

wherein:
- A is chosen from a monovalent group when n has the value zero or a polyvalent group when n is greater than or equal to 1, saturated or unsaturated, cyclic or non-cyclic and aromatic or non-aromatic hydrocarbon-based group comprising from 1 to 50 carbon atoms which is optionally interrupted with at least one or more heteroatom and/or optionally substituted, or a monovalent ($C_1$-$C_6$)alkyl group; or a polyvalent ($C_1$-$C_6$)alkylene group optionally substituted with at least one hydroxyl group;
- n is an integer ranging from 0 to 10;
- d) optionally, a fourth composition comprising at least one chemical oxidizing agent chosen from hydrogen peroxide, urea peroxide, or at least one hydrogen peroxide generating system; and
- e) optionally, a fifth composition comprising at least one basifying agent chosen from alkanolamines, carbonates, or bicarbonates;

wherein the first composition, the second composition, the third composition, the fourth composition, and/or the fifth composition are optionally identical;

wherein at least one composition chosen from the first composition, the second composition, the third composition, or the fourth composition has an acidic pH; and wherein the first composition, the second composition, the third composition, the fourth composition, and/or the fifth composition are aqueous or pulverulent; and at least one the first composition, the second composition, the third composition, the fourth composition, and/or the fifth composition is aqueous.

* * * * *